United States Patent
Loque

(10) Patent No.: US 10,920,231 B2
(45) Date of Patent: Feb. 16, 2021

(54) SYSTEMS AND METHODS FOR ENHANCING GENE EXPRESSION

(71) Applicant: The Regents of the University of California, Oakland, CA (US)

(72) Inventor: Dominique Loque, Albany, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/606,976

(22) Filed: Jan. 27, 2015

(65) Prior Publication Data

US 2015/0132809 A1 May 14, 2015

Related U.S. Application Data

(63) Continuation of application No. PCT/US2013/052578, filed on Jul. 29, 2013.

(60) Provisional application No. 61/676,811, filed on Jul. 27, 2012.

(51) Int. Cl.

| | |
|---|---|
| C07K 14/37 | (2006.01) |
| C07K 14/39 | (2006.01) |
| C07K 14/395 | (2006.01) |
| C12N 1/19 | (2006.01) |
| C12N 15/81 | (2006.01) |
| C12P 5/02 | (2006.01) |
| C12P 9/00 | (2006.01) |
| C12N 9/10 | (2006.01) |
| C12N 9/88 | (2006.01) |
| C12P 5/00 | (2006.01) |

(52) U.S. Cl.
CPC .......... *C12N 15/81* (2013.01); *C12N 9/1085* (2013.01); *C12N 9/88* (2013.01); *C12P 5/002* (2013.01); *C12P 9/00* (2013.01); *C12Y 205/01021* (2013.01); *C12Y 401/01033* (2013.01)

(58) Field of Classification Search
None
See application file for complete search history.

(56) References Cited

U.S. PATENT DOCUMENTS

| | | |
|---|---|---|
| 7,985,567 B2 | 7/2011 | Chou et al. |
| 2010/0170148 A1 | 7/2010 | Steen et al. |
| 2010/0180491 A1 | 7/2010 | Lee et al. |
| 2010/0305341 A1* | 12/2010 | Bailey .................. A23K 1/1612 549/512 |
| 2012/0115195 A1 | 5/2012 | Keasling et al. |
| 2013/0059295 A1 | 3/2013 | Chang et al. |
| 2013/0078683 A1 | 3/2013 | Loque et al. |

FOREIGN PATENT DOCUMENTS

| | | | |
|---|---|---|---|
| WO | 2006/014837 A1 | 2/2006 | |
| WO | WO 2006014837 A1 * | 2/2006 | ........... C12N 9/1085 |
| WO | 2012/064740 A1 | 5/2012 | |
| WO | 2012/103555 A2 | 8/2012 | |
| WO | 2012/135389 A2 | 10/2012 | |

OTHER PUBLICATIONS

Sayut et al., Construction and engineering of positive feedback loops, ACS Chem. Biol., 2006, 1, 692-96.*
Zhu et al., High-resolution DNA-binding specificity analysis of yeast transcription factors, Genome Res., 2009, 19, 556-66.*
Guo et al., Global gene expression profile of *Saccharomyces cerevisiae* induced by dictamnine, Yeast, 2008, 25, 631-41.*
Ro et al., Production of the antimalarial drug precursor artemisinic acid in engineered yeast, Nature, 2006, 440, 940-43.*
Hoot et al., The UPC2 Promoter in Candida albicans Contains Two cis-Acting Elements That Bind Directly to Upc2p, Resulting in Transcriptional Autoregulation, Eukaryotic Cell, 2010, 9, 1354-62.*
Guo et al., Protein tolerance to random amino acid change, Proc. Natl. Acad. Sci. USA, 2004, 101, 9205-10.*
International Search Report and Written Opinion of PCT/US2013/052578 dated Dec. 19, 2013. (Year: 2013).*
International Search Report and Written Opinion of PCT/US2013/052578 dated Dec. 19, 2013.
Nistala et al., "A modular positive feedback-based gene amplifier." J Biol Eng. 4:4 (2010), 8 pages.
Szostak et al., "Insertion of a genetic marker into the ribosomal DNA of yeast." Plasmid. 2(4):536-54 (1979).
Vik et al., "Upc2p and Ecm22p, Dual Regulators of Sterol Biosynthesis in *Saccharomyces cerevisiae*", Molecular and Cellular Biology, 21: 6395-6405 (2001).

* cited by examiner

*Primary Examiner* — Robert B Mondesi
*Assistant Examiner* — Todd M Epstein
(74) *Attorney, Agent, or Firm* — Robin C. Chiang; Lawrence Berkeley National Laboratory

(57) ABSTRACT

The present invention provides for a system for increasing the production of a compound using an artificial positive feedback loop (APFL). In some embodiments, the system diverts a compound produced in a first metabolic pathway into a second metabolic pathway in order to produce a compound of interest.

13 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 913
<212> TYPE: PRT
<213> ORGANISM: Saccharomyces cerevisiae

<400> SEQUENCE: 1

Met Ser Glu Val Gly Ile Gln Asn His Lys Lys Ala Val Thr Lys Pro
1               5                   10                  15

Arg Arg Arg Glu Lys Val Ile Glu Leu Ile Glu Val Asp Gly Lys Lys
            20                  25                  30

Val Ser Thr Thr Ser Thr Gly Lys Arg Lys Phe His Asn Lys Ser Lys
        35                  40                  45

Asn Gly Cys Asp Asn Cys Lys Arg Arg Val Lys Cys Asp Glu Gly
    50                  55                  60

Lys Pro Ala Cys Arg Lys Cys Thr Asn Met Lys Leu Glu Cys Gln Tyr
65                  70                  75                  80

Thr Pro Ile His Leu Arg Lys Gly Arg Gly Ala Thr Val Val Lys Tyr
                85                  90                  95
```

-continued

Val Thr Arg Lys Ala Asp Gly Ser Val Glu Ser Asp Ser Val Asp
            100                 105             110

Leu Pro Pro Thr Ile Lys Lys Glu Gln Thr Pro Phe Asn Asp Ile Gln
            115                 120             125

Ser Ala Val Lys Ala Ser Gly Ser Ser Asn Asp Ser Phe Pro Ser Ser
130             135                 140

Ala Ser Thr Thr Lys Ser Glu Ser Glu Glu Lys Ser Ser Ala Pro Ile
145             150                 155                 160

Glu Asp Lys Asn Asn Met Thr Pro Leu Ser Met Gly Leu Gln Gly Thr
                165             170             175

Ile Asn Lys Lys Asp Met Met Asn Asn Phe Phe Ser Gln Asn Gly Thr
            180                 185             190

Ile Gly Phe Gly Ser Pro Glu Arg Leu Asn Ser Gly Ile Asp Gly Leu
            195                 200             205

Leu Leu Pro Pro Leu Pro Ser Gly Asn Met Gly Ala Phe Gln Leu Gln
            210                 215             220

Gln Gln Gln Gln Val Gln Gln Ser Gln Pro Gln Thr Gln Ala Gln
225                 230             235             240

Gln Ala Ser Gly Thr Pro Asn Glu Arg Tyr Gly Ser Phe Asp Leu Ala
                245             250             255

Gly Ser Pro Ala Leu Gln Ser Thr Gly Met Ser Leu Ser Asn Ser Leu
            260                 265             270

Ser Gly Met Leu Leu Cys Asn Arg Ile Pro Ser Gly Gln Asn Tyr Thr
            275                 280             285

Gln Gln Gln Leu Gln Tyr Gln Leu His Gln Gln Leu Gln Leu Gln Gln
            290                 295             300

His Gln Gln Val Gln Leu Gln Gln Tyr Gln Gln Leu Arg Gln Glu Gln
305                 310             315             320

His Gln Gln Val Gln Gln Gln Gln Glu Gln Leu Gln Gln Tyr Gln
                325             330             335

Gln His Phe Leu Gln Gln Gln Gln Gln Val Leu Leu Gln Gln Glu Gln
            340                 345             350

Gln Pro Asn Asp Glu Glu Gly Gly Val Gln Glu Glu Asn Ser Lys Lys
            355                 360             365

Val Lys Glu Gly Pro Leu Gln Ser Gln Thr Ser Glu Thr Thr Leu Asn
370                 375             380

Ser Asp Ala Ala Thr Leu Gln Ala Asp Ala Leu Ser Gln Leu Ser Lys
385             390             395             400

Met Gly Leu Ser Leu Lys Ser Leu Ser Thr Phe Pro Thr Ala Gly Ile
                405             410             415

Gly Gly Val Ser Tyr Asp Phe Gln Glu Leu Leu Gly Ile Lys Phe Pro
            420                 425             430

Ile Asn Asn Gly Asn Ser Arg Ala Thr Lys Ala Ser Asn Ala Glu Glu
            435                 440             445

Ala Leu Ala Asn Met Gln Glu His His Glu Arg Ala Ala Ala Ser Val
            450                 455             460

Lys Glu Asn Asp Gly Gln Leu Ser Asp Thr Lys Ser Pro Ala Pro Ser
465             470                 475             480

Asn Asn Ala Gln Gly Gly Ser Ala Ser Ile Met Glu Pro Gln Ala Ala
                485             490             495

Asp Ala Val Ser Thr Met Ala Pro Ile Ser Met Ile Glu Arg Asn Met
            500                 505             510

```
Asn Arg Asn Ser Asn Ile Ser Pro Ser Thr Pro Ser Ala Val Leu Asn
            515                 520                 525

Asp Arg Gln Glu Met Gln Asp Ser Ile Ser Ser Leu Gly Asn Leu Thr
530                 535                 540

Lys Ala Ala Leu Glu Asn Asn Glu Pro Thr Ile Ser Leu Gln Thr Ser
545                 550                 555                 560

Gln Thr Glu Asn Glu Asp Asp Ala Ser Arg Gln Asp Met Thr Ser Lys
                565                 570                 575

Ile Asn Asn Glu Ala Asp Arg Ser Ser Val Ser Ala Gly Thr Ser Asn
            580                 585                 590

Ile Ala Lys Leu Leu Asp Leu Ser Thr Lys Gly Asn Leu Asn Leu Ile
            595                 600                 605

Asp Met Lys Leu Phe His His Tyr Cys Thr Lys Val Trp Pro Thr Ile
610                 615                 620

Thr Ala Ala Lys Val Ser Gly Pro Glu Ile Trp Arg Asp Tyr Ile Pro
625                 630                 635                 640

Glu Leu Ala Phe Asp Tyr Pro Phe Leu Met His Ala Leu Leu Ala Phe
                645                 650                 655

Ser Ala Thr His Leu Ser Arg Thr Glu Thr Gly Leu Glu Gln Tyr Val
            660                 665                 670

Ser Ser His Arg Leu Asp Ala Leu Arg Leu Leu Arg Glu Ala Val Leu
            675                 680                 685

Glu Ile Ser Glu Asn Asn Thr Asp Ala Leu Val Ala Ser Ala Leu Ile
            690                 695                 700

Leu Ile Met Asp Ser Leu Ala Asn Ala Ser Gly Asn Gly Thr Val Gly
705                 710                 715                 720

Asn Gln Ser Leu Asn Ser Met Ser Pro Ser Ala Trp Ile Phe His Val
                725                 730                 735

Lys Gly Ala Ala Thr Ile Leu Thr Ala Val Trp Pro Leu Ser Glu Arg
                740                 745                 750

Ser Lys Phe His Asn Ile Ile Ser Val Asp Leu Ser Asp Leu Gly Asp
            755                 760                 765

Val Ile Asn Pro Asp Val Gly Thr Ile Thr Glu Leu Val Cys Phe Asp
770                 775                 780

Glu Ser Ile Ala Asp Leu Tyr Pro Val Gly Leu Asp Ser Pro Tyr Leu
785                 790                 795                 800

Ile Thr Leu Ala Tyr Leu Asp Lys Leu His Arg Glu Lys Asn Gln Gly
                805                 810                 815

Asp Phe Ile Leu Arg Val Phe Thr Phe Pro Ala Leu Leu Asp Lys Thr
            820                 825                 830

Phe Leu Ala Leu Leu Met Thr Gly Asp Leu Gly Ala Met Arg Ile Met
            835                 840                 845

Arg Ser Tyr Tyr Lys Leu Leu Arg Gly Phe Ala Thr Glu Val Lys Asp
850                 855                 860

Lys Val Trp Phe Leu Glu Gly Val Thr Gln Val Leu Pro Gln Asp Val
865                 870                 875                 880

Asp Glu Tyr Ser Gly Gly Gly Met His Met Met Leu Asp Phe Leu
                885                 890                 895

Gly Gly Gly Leu Pro Ser Met Thr Thr Thr Asn Phe Ser Asp Phe Ser
            900                 905                 910

Leu

<210> SEQ ID NO 2
```

<211> LENGTH: 913
<212> TYPE: PRT
<213> ORGANISM: Saccharomyces cerevisiae

<400> SEQUENCE: 2

```
Met Ser Glu Val Gly Ile Gln Asn His Lys Lys Ala Val Thr Lys Pro
1               5                   10                  15

Arg Arg Arg Glu Lys Val Ile Glu Leu Ile Glu Val Asp Gly Lys Lys
                20                  25                  30

Val Ser Thr Thr Ser Thr Gly Lys Arg Lys Phe His Asn Lys Ser Lys
            35                  40                  45

Asn Gly Cys Asp Asn Cys Lys Arg Arg Val Lys Cys Asp Glu Gly
    50                  55                  60

Lys Pro Ala Cys Arg Lys Cys Thr Asn Met Lys Leu Glu Cys Gln Tyr
65                  70                  75                  80

Thr Pro Ile His Leu Arg Lys Gly Arg Gly Ala Thr Val Val Lys Tyr
                85                  90                  95

Val Thr Arg Lys Ala Asp Gly Ser Val Glu Ser Asp Ser Ser Val Asp
                100                 105                 110

Leu Pro Pro Thr Ile Lys Lys Glu Gln Thr Pro Phe Asn Asp Ile Gln
            115                 120                 125

Ser Ala Val Lys Ala Ser Gly Ser Ser Asn Asp Ser Phe Pro Ser Ser
    130                 135                 140

Ala Ser Thr Thr Lys Ser Glu Ser Glu Glu Lys Ser Ser Ala Pro Ile
145                 150                 155                 160

Glu Asp Lys Asn Asn Met Thr Pro Leu Ser Met Gly Leu Gln Gly Thr
                165                 170                 175

Ile Asn Lys Lys Asp Met Met Asn Asn Phe Phe Ser Gln Asn Gly Thr
                180                 185                 190

Ile Gly Phe Gly Ser Pro Glu Arg Leu Asn Ser Gly Ile Asp Gly Leu
            195                 200                 205

Leu Leu Pro Pro Leu Pro Ser Gly Asn Met Gly Ala Phe Gln Leu Gln
    210                 215                 220

Gln Gln Gln Gln Val Gln Gln Ser Gln Pro Gln Thr Gln Ala Gln
225                 230                 235                 240

Gln Ala Ser Gly Thr Pro Asn Glu Arg Tyr Gly Ser Phe Asp Leu Ala
                245                 250                 255

Gly Ser Pro Ala Leu Gln Ser Thr Gly Met Ser Leu Ser Asn Ser Leu
                260                 265                 270

Ser Gly Met Leu Leu Cys Asn Arg Ile Pro Ser Gly Gln Asn Tyr Thr
            275                 280                 285

Gln Gln Gln Leu Gln Tyr Gln Leu His Gln Gln Leu Gln Leu Gln Gln
    290                 295                 300

His Gln Gln Val Gln Leu Gln Tyr Gln Gln Leu Arg Gln Glu Gln
305                 310                 315                 320

His Gln Gln Val Gln Gln Gln Gln Glu Gln Leu Gln Tyr Gln
                325                 330                 335

Gln His Phe Leu Gln Gln Gln Gln Val Leu Leu Gln Gln Glu Gln
                340                 345                 350

Gln Pro Asn Asp Glu Glu Gly Gly Val Gln Glu Glu Asn Ser Lys Lys
            355                 360                 365

Val Lys Glu Gly Pro Leu Gln Ser Gln Thr Ser Glu Thr Thr Leu Asn
    370                 375                 380

Ser Asp Ala Ala Thr Leu Gln Ala Asp Ala Leu Ser Gln Leu Ser Lys
```

-continued

```
            385                 390                 395                 400
        Met Gly Leu Ser Leu Lys Ser Leu Ser Thr Phe Pro Thr Ala Gly Ile
                        405                 410                 415
        Gly Gly Val Ser Tyr Asp Phe Gln Glu Leu Leu Gly Ile Lys Phe Pro
                        420                 425                 430
        Ile Asn Asn Gly Asn Ser Arg Ala Thr Lys Ala Ser Asn Ala Glu Glu
                        435                 440                 445
        Ala Leu Ala Asn Met Gln Glu His His Glu Arg Ala Ala Ala Ser Val
                        450                 455                 460
        Lys Glu Asn Asp Gly Gln Leu Ser Asp Thr Lys Ser Pro Ala Pro Ser
        465                 470                 475                 480
        Asn Asn Ala Gln Gly Gly Ser Ala Ser Ile Met Glu Pro Gln Ala Ala
                        485                 490                 495
        Asp Ala Val Ser Thr Met Ala Pro Ile Ser Met Ile Glu Arg Asn Met
                        500                 505                 510
        Asn Arg Asn Ser Asn Ile Ser Pro Ser Thr Pro Ser Ala Val Leu Asn
                        515                 520                 525
        Asp Arg Gln Glu Met Gln Asp Ser Ile Ser Ser Leu Gly Asn Leu Thr
                        530                 535                 540
        Lys Ala Ala Leu Glu Asn Asn Glu Pro Thr Ile Ser Leu Gln Thr Ser
        545                 550                 555                 560
        Gln Thr Glu Asn Glu Asp Asp Ala Ser Arg Gln Asp Met Thr Ser Lys
                        565                 570                 575
        Ile Asn Asn Glu Ala Asp Arg Ser Ser Val Ser Ala Gly Thr Ser Asn
                        580                 585                 590
        Ile Ala Lys Leu Leu Asp Leu Ser Thr Lys Gly Asn Leu Asn Leu Ile
                        595                 600                 605
        Asp Met Lys Leu Phe His His Tyr Cys Thr Lys Val Trp Pro Thr Ile
                        610                 615                 620
        Thr Ala Ala Lys Val Ser Gly Pro Glu Ile Trp Arg Asp Tyr Ile Pro
        625                 630                 635                 640
        Glu Leu Ala Phe Asp Tyr Pro Phe Leu Met His Ala Leu Leu Ala Phe
                        645                 650                 655
        Ser Ala Thr His Leu Ser Arg Thr Glu Thr Gly Leu Glu Gln Tyr Val
                        660                 665                 670
        Ser Ser His Arg Leu Asp Ala Leu Arg Leu Leu Arg Glu Ala Val Leu
                        675                 680                 685
        Glu Ile Ser Glu Asn Asn Thr Asp Ala Leu Val Ala Ser Ala Leu Ile
                        690                 695                 700
        Leu Ile Met Asp Ser Leu Ala Asn Ala Ser Gly Asn Gly Thr Val Gly
        705                 710                 715                 720
        Asn Gln Ser Leu Asn Ser Met Ser Pro Ser Ala Trp Ile Phe His Val
                        725                 730                 735
        Lys Gly Ala Ala Thr Ile Leu Thr Ala Val Trp Pro Leu Ser Glu Arg
                        740                 745                 750
        Ser Lys Phe His Asn Ile Ile Ser Val Asp Leu Ser Asp Leu Gly Asp
                        755                 760                 765
        Val Ile Asn Pro Asp Val Gly Thr Ile Thr Glu Leu Val Cys Phe Asp
                        770                 775                 780
        Glu Ser Ile Ala Asp Leu Tyr Pro Val Gly Leu Asp Ser Pro Tyr Leu
        785                 790                 795                 800
        Ile Thr Leu Ala Tyr Leu Asp Lys Leu His Arg Glu Lys Asn Gln Gly
                        805                 810                 815
```

```
Asp Phe Ile Leu Arg Val Phe Thr Phe Pro Ala Leu Leu Asp Lys Thr
                820                 825                 830

Phe Leu Ala Leu Leu Met Thr Gly Asp Leu Gly Ala Met Arg Ile Met
            835                 840                 845

Arg Ser Tyr Tyr Lys Leu Leu Arg Gly Phe Ala Thr Glu Val Lys Asp
        850                 855                 860

Lys Val Trp Phe Leu Glu Gly Val Thr Gln Val Leu Pro Gln Asp Val
865                 870                 875                 880

Asp Glu Tyr Ser Gly Gly Asp Met His Met Met Leu Asp Phe Leu
                885                 890                 895

Gly Gly Gly Leu Pro Ser Met Thr Thr Thr Asn Phe Ser Asp Phe Ser
                900                 905                 910

Leu

<210> SEQ ID NO 3
<211> LENGTH: 814
<212> TYPE: PRT
<213> ORGANISM: Candida albicans

<400> SEQUENCE: 3

Met Thr Ser Asp Asp Gly Asn Ala Gly Gln Glu Arg Glu Lys Asp Ala
1               5                   10                  15

Glu Leu Ile Glu Val Gly Gly Lys Lys Val Ser Lys Thr Ser Thr Gly
                20                  25                  30

Lys Arg Lys Phe His Asn Lys Ser Lys Thr Gly Cys Asp Asn Cys Lys
            35                  40                  45

Arg Arg Arg Val Lys Cys Asp Glu Gly Lys Pro Phe Cys Lys Lys Cys
        50                  55                  60

Thr Asn Met Lys Leu Asp Cys Val Tyr Ser Pro Ile Gln Pro Arg Arg
65                  70                  75                  80

Arg Lys Asp Ser Ser Ser Lys Phe Ala Ser Ala Val His Asp Arg
                85                  90                  95

Val Gly Lys Lys Asn Leu Ser Asp Asn Ala Ile Met Leu Gln Gln Gln
            100                 105                 110

Gln Gln Gln Leu His His Gln Gln Glu Gln Gln Phe Arg Gln Gln Gln
        115                 120                 125

Gln Val Gln Leu Gln Gln Leu Leu Pro His Val Gly Thr Asp Glu
    130                 135                 140

Gln Ser Asn Ser Pro Asn Ser Val Pro Pro Ser Val Ser Asn Asn Met
145                 150                 155                 160

Glu Asn Leu Leu Leu Pro His Leu Leu Ala Ser Leu Val Asn Thr
                165                 170                 175

Ser Asn Ser Thr Asn Ser Ser Ala Asn Gly Ala Glu Ala His Asn Asn
            180                 185                 190

Ile Thr Gln Thr Ala Pro Ser Ser Met Ile Asn Asn Asn His Pro Asn
        195                 200                 205

Met Ala Leu Pro Gly Asn Ser Pro Leu Ser Ile Pro Ile Thr Pro Ser
    210                 215                 220

Phe Gln Ser Thr Ala Met Asn Leu Ser Ser Ser Leu Asn Gly Leu Leu
225                 230                 235                 240

Ser Pro Gly Arg Leu Asn Ser Val Thr Asn Gly Leu Gln Gln Pro Gln
                245                 250                 255

Leu Gln Gln Gln Asn Gln Gln Ile Pro Gln Gln Gln Gly Thr Gln Ser
            260                 265                 270
```

```
Pro Phe Ser Asn Ile Pro Phe Asp Gln Leu Ala Gln Leu Asn Lys Met
    275                 280                 285

Gly Leu Asn Phe Asn Met Lys Ser Phe Asn Thr Leu Phe Pro Tyr Gly
    290                 295                 300

Ala Ala Asn Gly Met Ala Ser Glu Phe Gln Glu Leu Phe Gly Leu Gly
305                 310                 315                 320

Lys Phe Ala Thr Ser Asn Asn Arg Ala Ile Lys Val Ser Thr Ala Glu
                325                 330                 335

Glu Ala Leu Ala Asn Met Gln Gln Glu Gln Glu Asp Lys Asn Lys Gln
                340                 345                 350

Phe Thr Lys Asn Pro Leu Asp Asn Thr Lys Thr Asp Ala Val Asn Ser
            355                 360                 365

Gly Asn Asn Pro Leu Asn Gly Asn Glu Asn Lys Val Thr Ala Ser Asp
    370                 375                 380

Ile Leu Ser His Asn Lys Asn Leu Ile Ile Asp Asn Thr Gly Leu Thr
385                 390                 395                 400

Ile Ser Pro Pro His Thr Leu Ser Lys Pro Ser Ile Asp Gln Asn Ile
                405                 410                 415

Ala Ser Pro Ser Thr Gly Val Ser Asn Val Thr Ser Thr Lys Ser Leu
            420                 425                 430

Leu Ser Ile Pro Asp Asn Arg Thr Ala Leu Gly Asn Ser Pro Thr Leu
            435                 440                 445

Lys Thr Ser Pro Met Gly Asp Leu Leu Ser Asn Ser Glu Ala Leu Ser
        450                 455                 460

Pro Arg Ser Ser Asn Ser His Thr Gln Gln Gln Ser Ser Pro His Ser
465                 470                 475                 480

Asn Ala Ser Ser Ala Ser Arg Leu Val Pro Glu Leu Val Gly Leu Ser
                485                 490                 495

Arg Lys Ser Asn Leu Asn Leu Ile Asp Leu Lys Leu Phe His His Tyr
                500                 505                 510

Cys Thr Asp Val Trp His Thr Ile Thr Glu Ala Gly Ile Ser Gly Pro
            515                 520                 525

Glu Val Trp Ser Thr Tyr Ile Pro Asp Leu Ala Phe His Phe Pro Phe
        530                 535                 540

Leu Met His Thr Ile Leu Ala Phe Ser Ala Thr His Leu Ser Arg Thr
545                 550                 555                 560

Glu Ala Gly Leu Asp Asn Tyr Val Ser Ser His Arg Leu Glu Ala Leu
                565                 570                 575

Arg Leu Leu Arg Glu Ala Val Leu Glu Ile Ser Asp Asp Asn Thr Asp
                580                 585                 590

Ala Leu Val Ala Ser Ala Leu Ile Leu Ile Leu Asp Ser Leu Ala Asn
            595                 600                 605

Ala Ser Ser Ser Pro Thr Ala Trp Ile Phe His Val Lys Gly Ala
    610                 615                 620

Val Thr Ile Leu Thr Ala Val Trp Pro Leu Ser Glu Thr Ser Lys Phe
625                 630                 635                 640

Tyr Asn Leu Ile Ser Val Asp Leu Ser Asp Leu Gly Glu Ala Val Ile
                645                 650                 655

Asn Gln Ser Asn His Asn Asn Asp Asp Asn Ser Asn Asn Gly Asp
                660                 665                 670

Gly Asn Asn Asn Thr Ile Ser Glu Leu Val Cys Phe Asp Glu Ser
    675                 680                 685
```

```
Ile Ala Asp Leu Tyr Pro Val Glu Ile Asp Ser Pro Tyr Leu Ile Thr
    690                 695                 700

Leu Ala Tyr Leu Asp Lys Leu His Arg Glu Lys Asn Gln Leu Asp Phe
705                 710                 715                 720

Met Leu Arg Val Phe Ser Phe Pro Ala Leu Leu Asp Arg Thr Phe Leu
                725                 730                 735

Ala Leu Leu Met Thr Gly Asp Leu Gly Ala Met Arg Ile Met Arg Ser
            740                 745                 750

Tyr Tyr Thr Leu Leu Arg Gly Tyr Thr Thr Glu Ile Lys Asp Lys Val
                755                 760                 765

Trp Phe Leu Asp Ser Val Ser Gln Val Leu Pro Gln Asp Val Asp Glu
770                 775                 780

Tyr Ser Gly Gly Gly Met His Met Met Leu Asp Phe Leu Gly Gly
785                 790                 795                 800

Gly Leu Pro Ser Met Thr Thr Thr Asn Phe Ser Ala Phe Met
                805                 810
```

<210> SEQ ID NO 4
<211> LENGTH: 814
<212> TYPE: PRT
<213> ORGANISM: Candida albicans

<400> SEQUENCE: 4

```
Met Thr Ser Asp Asp Gly Asn Ala Gly Gln Glu Arg Glu Lys Asp Ala
1               5                   10                  15

Glu Leu Ile Glu Val Gly Gly Lys Lys Val Ser Lys Thr Ser Thr Gly
                20                  25                  30

Lys Arg Lys Phe His Asn Lys Ser Lys Thr Gly Cys Asp Asn Cys Lys
            35                  40                  45

Arg Arg Arg Val Lys Cys Asp Glu Gly Lys Pro Phe Cys Lys Lys Cys
50                  55                  60

Thr Asn Met Lys Leu Asp Cys Val Tyr Ser Pro Ile Gln Pro Arg Arg
65                  70                  75                  80

Arg Lys Asp Ser Ser Ser Lys Phe Ala Ser Ala Val His Asp Arg
                85                  90                  95

Val Gly Lys Lys Asn Leu Ser Asp Asn Ala Ile Met Leu Gln Gln
                100                 105                 110

Gln Gln Gln Leu His His Gln Gln Glu Gln Gln Phe Arg Gln Gln Gln
        115                 120                 125

Gln Val Gln Leu Gln Gln Leu Leu Pro His Val Gly Thr Asp Glu
    130                 135                 140

Gln Ser Asn Ser Pro Asn Ser Val Pro Pro Ser Val Ser Asn Asn Met
145                 150                 155                 160

Glu Asn Leu Leu Leu Pro His Leu Leu Ala Ser Leu Val Asn Asn Thr
                165                 170                 175

Ser Asn Ser Thr Asn Ser Ser Ala Asn Gly Ala Glu Ala His Asn Asn
                180                 185                 190

Ile Thr Gln Thr Ala Pro Ser Ser Met Ile Asn Asn Asn His Pro Asn
            195                 200                 205

Met Ala Leu Pro Gly Asn Ser Pro Leu Ser Ile Pro Ile Thr Pro Ser
    210                 215                 220

Phe Gln Ser Thr Ala Met Asn Leu Ser Ser Leu Asn Gly Leu Leu
225                 230                 235                 240

Ser Pro Gly Arg Leu Asn Ser Val Thr Asn Gly Leu Gln Gln Pro Gln
                245                 250                 255
```

-continued

Leu Gln Gln Gln Asn Gln Ile Pro Gln Gln Gly Thr Gln Ser
            260                 265             270

Pro Phe Ser Asn Ile Pro Phe Asp Gln Leu Ala Gln Leu Asn Lys Met
            275                 280             285

Gly Leu Asn Phe Asn Met Lys Ser Phe Asn Thr Leu Phe Pro Tyr Gly
290                 295                 300

Ala Ala Asn Gly Met Ala Ser Glu Phe Gln Glu Leu Phe Gly Leu Gly
305                 310                 315                 320

Lys Phe Ala Thr Ser Asn Asn Arg Ala Ile Lys Val Ser Thr Ala Glu
                325                 330                 335

Glu Ala Leu Ala Asn Met Gln Gln Glu Gln Asp Lys Asn Lys Gln
            340                 345                 350

Phe Thr Lys Asn Pro Leu Asp Asn Thr Lys Thr Asp Ala Val Asn Ser
            355                 360                 365

Gly Asn Asn Pro Leu Asn Gly Asn Glu Asn Lys Val Thr Ala Ser Asp
370                 375                 380

Ile Leu Ser His Asn Lys Asn Leu Ile Ile Asp Asn Thr Gly Leu Thr
385                 390                 395                 400

Ile Ser Pro Pro His Thr Leu Ser Lys Pro Ser Ile Asp Gln Asn Ile
                405                 410                 415

Ala Ser Pro Ser Thr Gly Val Ser Asn Val Thr Ser Thr Lys Ser Leu
            420                 425                 430

Leu Ser Ile Pro Asp Asn Arg Thr Ala Leu Gly Asn Ser Pro Thr Leu
            435                 440                 445

Lys Thr Ser Pro Met Gly Asp Leu Leu Ser Asn Ser Glu Ala Leu Ser
    450                 455                 460

Pro Arg Ser Ser Asn Ser His Thr Gln Gln Ser Ser Pro His Ser
465                 470                 475                 480

Asn Ala Ser Ser Ala Ser Arg Leu Val Pro Glu Leu Val Gly Leu Ser
                485                 490                 495

Arg Lys Ser Asn Leu Asn Leu Ile Asp Leu Lys Leu Phe His His Tyr
            500                 505                 510

Cys Thr Asp Val Trp His Thr Ile Thr Glu Ala Gly Ile Ser Gly Pro
            515                 520                 525

Glu Val Trp Ser Thr Tyr Ile Pro Asp Leu Ala Phe His Phe Pro Phe
    530                 535                 540

Leu Met His Thr Ile Leu Ala Phe Ser Ala Thr His Leu Ser Arg Thr
545                 550                 555                 560

Glu Ala Gly Leu Asp Asn Tyr Val Ser Ser His Arg Leu Glu Ala Leu
                565                 570                 575

Arg Leu Leu Arg Glu Ala Val Leu Glu Ile Ser Asp Asp Asn Thr Asp
            580                 585                 590

Ala Leu Val Ala Ser Ala Leu Ile Leu Ile Leu Asp Ser Leu Ala Asn
            595                 600                 605

Ala Ser Ser Ser Ser Pro Thr Ala Trp Ile Phe His Val Lys Gly Ala
    610                 615                 620

Val Thr Ile Leu Thr Ala Val Trp Pro Leu Ser Glu Thr Ser Lys Phe
625                 630                 635                 640

Tyr Asn Leu Ile Ser Val Asp Leu Ser Asp Leu Gly Glu Ala Val Ile
                645                 650                 655

Asn Gln Ser Asn His Asn Asn Asp Asn Asp Asn Ser Asn Asn Gly Asp
            660                 665                 670

```
Gly Asn Asn Asn Asn Thr Ile Ser Glu Leu Val Cys Phe Asp Glu Ser
    675             680             685

Ile Ala Asp Leu Tyr Pro Val Glu Ile Asp Ser Pro Tyr Leu Ile Thr
690             695             700

Leu Ala Tyr Leu Asp Lys Leu His Arg Glu Lys Asn Gln Leu Asp Phe
705             710             715             720

Met Leu Arg Val Phe Ser Phe Pro Ala Leu Leu Asp Arg Thr Phe Leu
                725             730             735

Ala Leu Leu Met Thr Gly Asp Leu Gly Ala Met Arg Ile Met Arg Ser
            740             745             750

Tyr Tyr Thr Leu Leu Arg Gly Tyr Thr Thr Glu Ile Lys Asp Lys Val
        755             760             765

Trp Phe Leu Asp Ser Val Ser Gln Val Leu Pro Gln Asp Val Asp Glu
    770             775             780

Tyr Ser Gly Gly Gly Asp Met His Met Met Leu Asp Phe Leu Gly Gly
785             790             795             800

Gly Leu Pro Ser Met Thr Thr Thr Asn Phe Ser Ala Phe Met
            805             810
```

SYSTEMS AND METHODS FOR ENHANCING GENE EXPRESSION

CROSS-REFERENCE TO RELATED APPLICATIONS

This application claims priority as a continuation application to PCT International Patent application No. PCT/US13/52578, filed Jul. 29, 2013, which claims priority to U.S. Provisional Patent Application Ser. No. 61/676,811, filed on Jul. 27, 2012, both of which are hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of gene expression in fungi.

BACKGROUND OF THE INVENTION

Plant engineering has led to a technology that enables one skilled on the art to enhance gene expression and metabolic pathways in specific tissues and/or at specific developmental stages (see PCT International Patent Application No.: PCT/US2012/023182, Loqué and Scheller, Spatially Modified Gene Expression in Plants).

This technology is based on the creation of an artificial positive feedback loop (APFL) and is achieved by inserting in the genome an engineered gene consisting of specific promoter and the encoding sequence of a selected transcription factor. When induced, the APFL allows the overexpression and self-expression maintenance of selected transcription factors and consequently enhances transcription activity of downstream promoters associated to this pathway to higher level than the native control. APFL can also be used to alleviate undesired side-effects caused by the overexpression in non-target cells since it retains spatial expression.

The since APFL enhances activity of several promoters (promoters belonging to the induced pathway), it means that most of these promoters can be used to engineer a metabolic pathway to be highly expressed at the same time as the "APFL dependent pathway".

In fungi, there are several transcriptions factors identified known to induce particular metabolic pathways and so far the over-expression depends on the isolation of strong promoters and the use of high copy plasmids. Unfortunately, approaches using high copy plasmids strategies are rarely very stable and the number of strong promoters with the right expression patterns is also limiting and they are not always transferable between fungi.

The current approaches use high copy plasmid and/or "strong"/constitutive promoters to express the genes of engineered pathways and transcription factors. In contrast to many other strategies, the "self-over-induction" of transcription factors caused by APFL and the used of induced promoters for the pathway engineering will allow higher yield of target molecules and does not require the use of plasmid and offers higher success for stable overexpression of metabolic pathways.

SUMMARY OF THE INVENTION

The present invention provides for a system for increasing the production of a compound using an artificial positive feedback loop (APFL). The system is a fungal host cell, or a cell-free system comprising, such as a fungal cell extract. In some embodiments, the system diverts a compound produced in a first metabolic pathway into a second metabolic pathway in order to produce a compound of interest.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
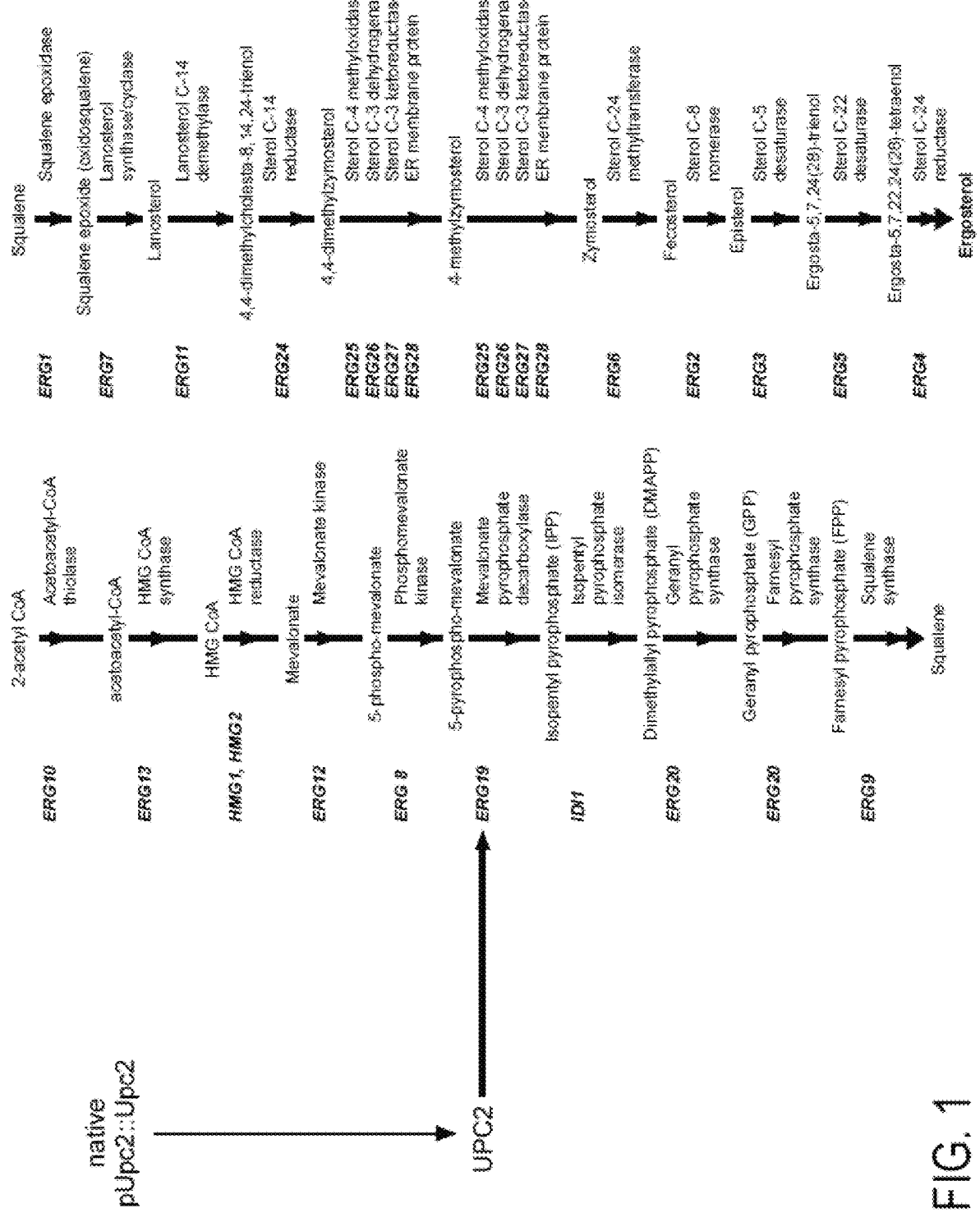
FIG. 1 shows the native system/regulation in yeast to produce farnesyl diphosphate (FPP) and ergosterol.
Figure 2:
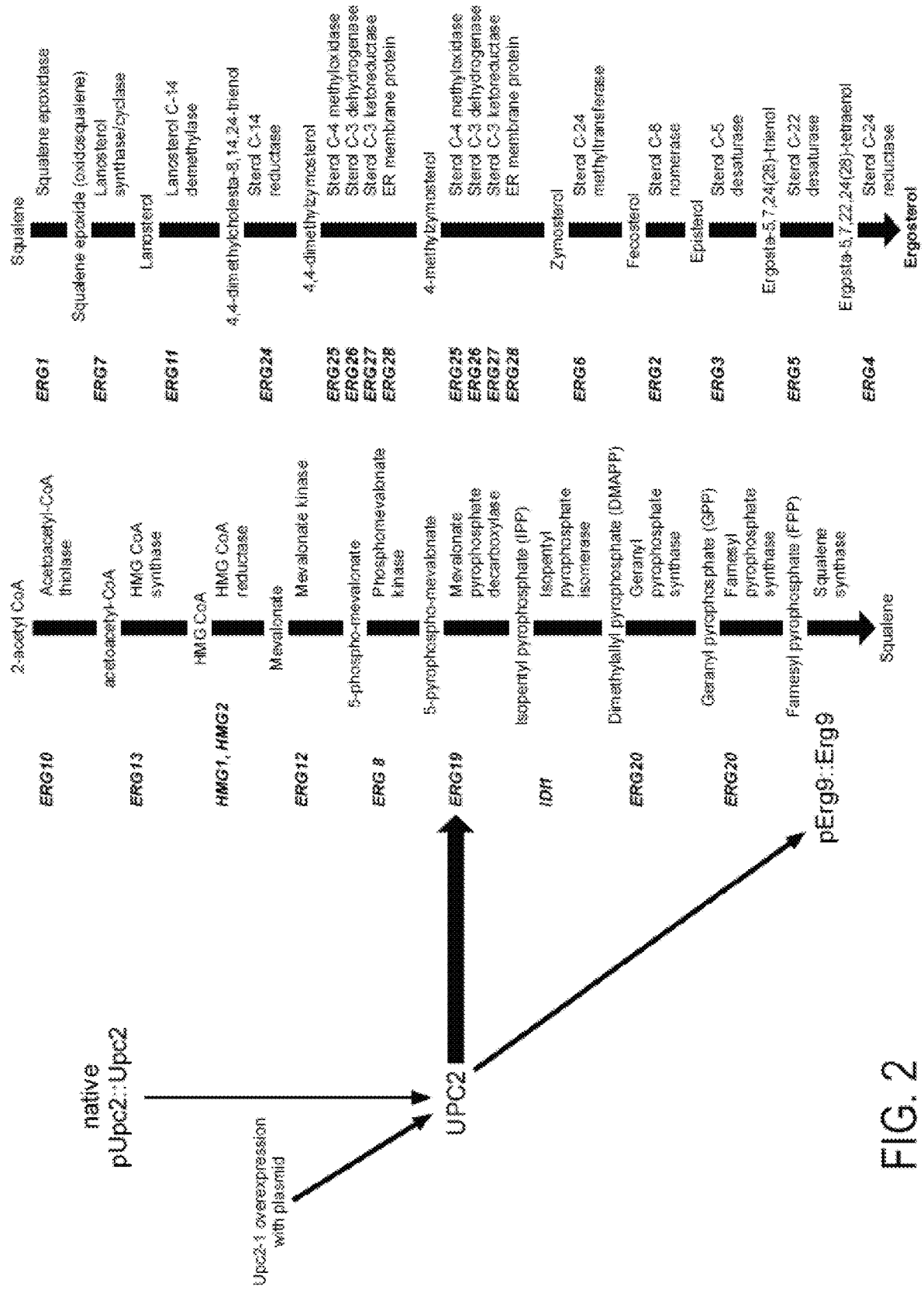
FIG. 2 shows a conventional overexpression of transcription factors in yeast. The example here is UPC2, a known transcription factor that regulates ergosterol biosynthesis.
Figure 3:
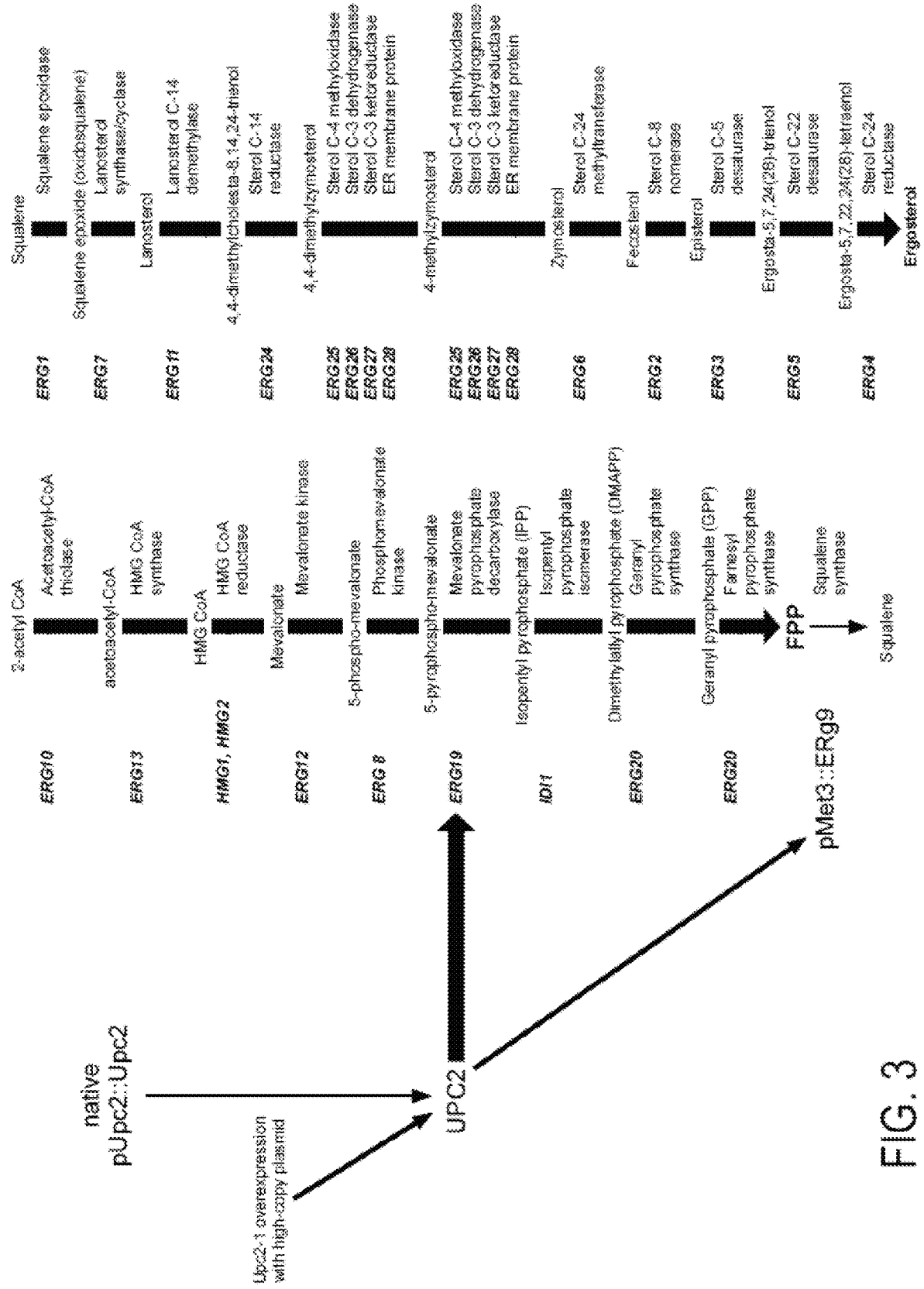
FIG. 3 shows the conventional overexpression with current approach to increase FPP availability in yeast.
Figure 4:
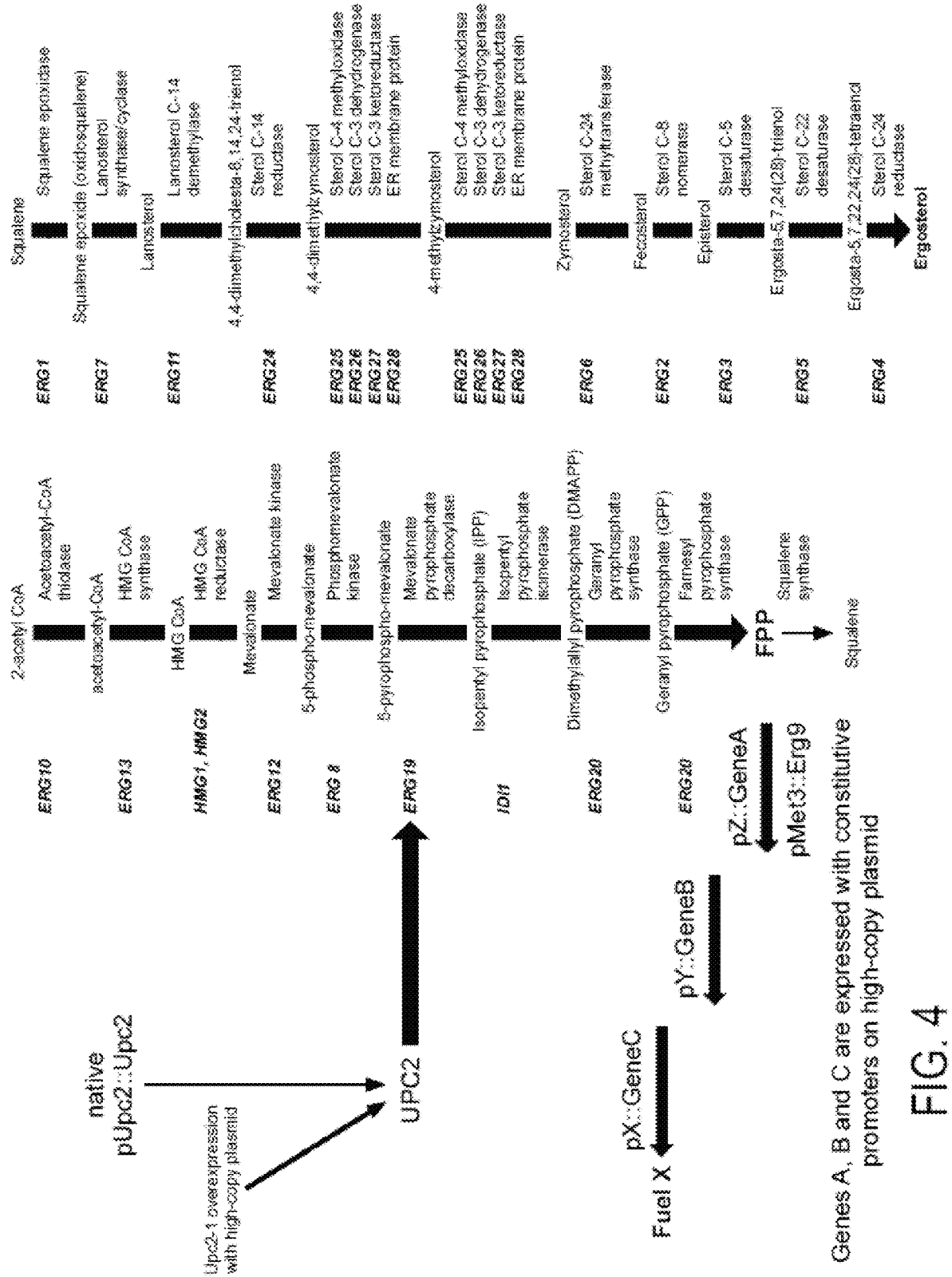
FIG. 4 shows the conventional overexpression with current approach to increase FPP availability in yeast and an engineered pathway to produce a fuel X.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "heterologous" as used herein refers to describe when two elements (such as promoter and an open reading frame (ORF) are not naturally found to be physically or covalently linked to each other, or when a gene or other genetic element is not naturally found in a species of organism.

The term "native" as used herein refers to describe when two elements (such as promoter and an open reading frame (ORF) are naturally found to be physically or covalently linked to each other, or when a gene or other genetic element is naturally found in a species of organism.

As used herein, the terms "polynucleotide", "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "functional variant" refers to a protein, such as an enzyme or transcription factor, that has an amino acid sequence that is at least 70%, 75%, 80%, 85%, 90%, 95% or 99% identical to the amino acid sequence of any one of the proteins described in this specification or in an incorporated reference. The functional variant retains amino acids residues that are recognized as conserved for the protein. The functional variant may have non-conserved amino acid residues replaced or found to be of a different amino acid, or amino acid(s) inserted or deleted, but which does not affect or has insignificant effect on the enzymatic activity of the functional variant. The functional variant has an enzymatic or biological activity that is identical or essentially identical to the enzymatic or biological activity any one of the proteins described in this specification or in an incorporated reference. The functional variant may be found in nature or be an engineered mutant thereof. The mutant may have one or more amino acids substituted, deleted or inserted, or a combination thereof, as compared to the protein described in this specification or in an incorporated reference. The term "functional variant" can also refer to a nucleotide sequence, such as a promoter, that has a nucleotide sequence that is at least 70%, 75%, 80%, 85%, 90%, 95% or 99% identical to the nucleotide sequence of any one of the nucleotide sequence, such as a promoter, described in this specification or in an incorporated reference.

The present invention provides a system for producing a first compound or compound of interest, comprising: (a) a first polynucleotide encoding a fungal transcription factor, or functional variant thereof, operably linked to a first promoter that is induced or activated by the transcription factor, wherein the first promoter is heterologous to the transcription factor, (b) a second polynucleotide encoding a first biosynthetic enzyme operably linked to a second promoter that is induced or activated by the transcription factor, wherein the first biosynthetic enzyme catalyzes a first reaction which produces the first compound from a second compound, and the second promoter is heterologous to the first biosynthetic enzyme, and (c) a third polynucleotide encoding a second biosynthetic enzyme operably linked to a third promoter that is weakly induced (i.e., induced or activated a level lower than the induction or activation of the first and/or second promoters), not induced, or repressed by the transcription factor, wherein the second biosynthetic enzyme catalyzes a second reaction that converts the second compound into a third compound, and the third promoter is heterologous to the second biosynthetic enzyme. The present invention provides a genetically modified yeast host cell comprising the system of the present invention.

In some embodiments, the first and second promoters have the identical or substantially identical nucleotide sequences. In some embodiments, the second biosynthetic enzyme is native to the host cell, and the host cell has been genetically modified to replace or substitute the native promoter of the second biosynthetic enzyme with the third promoter. In some embodiments, the native promoter of the second biosynthetic enzyme is the first or second promoter. In some embodiments, the host cell has been genetically modified to reduce expression of a biosynthetic enzyme (which is an enzyme in a metabolic pathway) in order to divert the precursor of the biosynthetic enzyme from a first metabolic pathway into a second metabolic pathway in order to produce a compound of interest, wherein optionally the second metabolic pathway is heterologous to the host cell, to yeast, or to eukaryotes. In some embodiments, the second metabolic pathway is derived or obtained from a bacterium. In some embodiments, the first and third polynucleotides are the same polynucleotide, such as a chromosome of the host cell. In some embodiments, the host cell is modified by inserting a polynucleotide heterologous to the host cell comprising in a 5' to 3' sequence the following: an open reading frame (ORF) encoding the transcription factor, one or more terminators, a promoter that is weakly induced, not induced, or repressed by the transcription factor, between the native promoter of a biosynthetic enzyme and the ORF of the biosynthetic enzyme on a chromosome of the host cell, such that the native promoter of the biosynthetic enzyme is operatively linked to the ORF) encoding the transcription factor, and the promoter that is weakly induced, not induced, or repressed by the transcription factor is operatively linked to the biosynthetic enzyme, wherein the native promoter of a biosynthetic enzyme is induced or activated by the transcription factor. In some embodiments, the host cell is further genetically modified to comprise a polynucleotide encoding one or more biosynthetic enzymes each operably linked to a promoter (each optionally induced or activated by the transcription factor), wherein the one or more biosynthetic enzymes catalyze one or a series of reactions wherein the precursor is catalyzed into a compound of interest.

In some embodiments, the system further comprises one or more polynucleotides encoding further biosynthetic enzymes, each operably linked to a promoter as described comprised by the third polynucleotide, wherein each further biosynthetic enzyme catalyzes a reaction in a metabolic or biosynthetic pathway involving the first compound. In some embodiments, the system further comprises a polynucleotide encoding the transcription factor operably linked to a promoter capable of expressing the transcription factor, such as the promoter native to the transcription factor. In some embodiments, the transcription factor is capable of inducing or activating the expression of one or more enzymes that catalyze the biosynthesis of the precursors of the first compound of a first pathway. In some embodiments, the transcription factor is capable of inducing or activating the expression of one or more enzymes that catalyze the biosynthesis of a final compound or compound of interest of a second metabolic pathway wherein the first or second compound is a precursor in the biosynthesis of the final compound or compound of interest in a second pathway. The transcription factor can be either native or heterologous to the host cell.

The present invention provides for a system for producing a compound comprising: (a) a first polynucleotide encoding a fungal transcription factor, or functional variant thereof, operably linked to a heterologous promoter, wherein the transcription factor induces expression from the heterologous promoter, (b) a second polynucleotide encoding a first biosynthetic enzyme operably linked to the heterologous promoter, wherein the first biosynthetic enzyme catalyzes a first reaction which produces the compound, and (c) optionally a third polynucleotide encoding a second biosynthetic enzyme operably linked to a promoter that is weakly induced, not induced, or repressed by the transcription factor, wherein the second biosynthetic enzyme catalyzes a second reaction that converts a precursor of the compound into another compound.

When the system is in a yeast host cell, the yeast host cell is a genetically modified host cell. When the system is in a yeast host cell, the first pathway is native or heterologous o the host cell. In some embodiments, the second pathway is heterologous to the host cell.

In some embodiments, any two or all of the first polynucleotide, second nucleotide, and third polynucleotide are the same polynucleotide. In some embodiments, the system is in a host cell and any of the polynucleotide can be a chromosome of the host cell.

The present invention provides for a nucleic acid comprising a polynucleotide encoding, from 5' to 3', a transcription factor, one or more terminators, and a second promoter that is weakly induced (i.e., induced or activated a level lower than the induction or activation of a promoter that is induced by the transcription factor in nature), not induced, or repressed by the transcription factor; wherein the nucleic acid is capable of insertion into another polynucleotide between a first promoter and an open reading frame (ORF) of a protein that is operably linked to the first promoter in nature. The present invention provides for a polynucleotide inserted as described above.

In some embodiments, the transcription factor is a fungal transcription factor comprising a GAL4-like Zn2Cys6 binuclear cluster DNA-binding domain. The GAL4-like Zn2Cys6 binuclear cluster DNA-binding domain comprises two helices organized around a Zn(2)Cys(6) motif, and is capable of binding to sequences comprising 2 DNA half sites comprised of 3-5 C/G combinations.

In some embodiments, the transcription factor is a yeast transcription factor. In some embodiments, the transcription factor is a transcription factor from a yeast of the genus *Saccharomyces* or *Candida*. In some embodiments, the transcription factor is a *Saccharomyces cerevisiae* transcription factor. In some embodiments, the transcription factor is a *Candida albicans* transcription factor.

In some embodiments, the transcription factor is Upc2, Ecm22, Upc2G888D, or Ecm22G790D, or a functional variant thereof.

The amino acid sequence of Upc2 (*Saccharomyces cerevisiae* S288c) is as follows:

(SEQ ID NO: 1)
```
  1 msevgiqnhk kavtkprrre kvielievdg kkvsttstgk rkfhnkskng cdnckrrrvk 61 cdegkpacrk ctnmklecqy tpihlrkgrg atvvkyvtrk adgsvesdss vdlpptikke 121 qtpfndiqsa vkasgssnds fpssasttks eseekssapi edknnmtpls mglqgtinkk 181 dmmnnffsqn gtigfgsper lnsgidglll pplpsgnmga fqlqqqqqvg qqsqpqtqaq
```

```
241 qasgtpnery gsfdlagspa lqstgmslsn slsgmllcnr ipsgqnytqq qlqyqlhqql 301 qlqqhqqvql qqyqqlrqeq hqqvqqqqqe lqqyqqhfl qqqqqvllqq eqqpndeegg 361 vqeenskkvk egplgsqtse ttlnsdaatl qadalsqlsk mglslkslst fptagiggvs 421 ydfqellgik fpinngnsra tkasnaeeal anmqehhera aasvkendgq lsdtkspaps 481 nnaqggsasi mepqaadays tmapismier nmnrnsnisp stpsavindr qemqdsissl 541 gnltkaalen neptislqts qteneddasr qdmtskinne adrssysagt sniaklldls 601 tkgnlnlidm klfhhyctkv wptitaakvs gpeiwrdyip elafdypflm hallafsath 661 lsrtetgleq yvsshrldal rllreavlei senntdalva salilimdsl anasgngtvg 721 nqslnsmsps awifhvkgaa tiltavwpls erskfhniis vdlsdlgdvi npdvgtitel 781 vcfdesiadl ypvgldspyl itlayldklh reknqgdfil rvftfpalld ktflallmtg 841 dlgamrimrs yykllrgfat evkdkvwfle gvtqvlpqdv deysggggmh mmldflgggl 901 psmtttnfsd fsl
```

The amino acid sequence of Upc2G888D is identical to that of SEQ ID NO:1, except the G at position 888 is substituted with D (SEQ ID NO:2).

The amino acid sequence of Ecm22 (*Candida albicans*) is as follows:

```
                                                        (SEQ ID NO: 3)
  1 mtsddgnagq erekdaelie vggkkvskts tgkrkfhnks ktgcdnckrr rvkcdegkpf 61 ckkctnmkld cvyspiqprr rkdsssskfa savhdrvgkk nlsdnaimlq qqqqqlhhqq 121 eqqfrqqqqv qlqqqllphv gtdeqsnspn svppsvsnnm enlllphlla slvnntsnst 181 nssangaeah nnitqtapss minnnhpnma lpgnsplsip itpsfqstam nlssslngll 241 spgrinsvtn glqqpqlqqq nqqipqqqgt qspfsnipfd qlaqlnkmgl nfnmksfntl 301 fpygaangma sefqelfglg kfatsnnrai kvstaeeala nmqqeqedkn kqftknpldn 361 tktdavnsgn nplngnenkv tasdilshnk nliidntglt ispphtlskp sidqniasps 421 tgvsnvtstk sllsipdnrt algnsptlkt spmgdllsns ealsprssns htqqqssphs 481 nassasrlvp elvglsrksn lnlidlklfh hyctdvwhti teagisgpev wstyipdlaf 541 hfpflmhtil afsathlsrt eagldnyvss hrlealrllr eavleisddn tdalvasali 601 lildslanas sssptawifh vkgavtilta vwplsetskf ynlisvdlsd lgeavinqsn 661 hnndndnsnn gdgnnnntis elvcfdesia dlypveidsp ylitlayldk lhreknqldf 721 mlrvfsfpal ldrtflallm tgdlgamrim rsyytllrgy tteikdkvwf ldsysqvlpq 781 dvdeysgggg mhmmldflgg glpsmtttnf safm
```

The amino acid sequence of Ecm22G790D is identical to that of SEQ ID NO:3, except the G at position 790 is substituted with D (SEQ ID NO:4).

In some embodiments, the heterologous promoter is the erg9 promoter, or functional variant thereof. In some embodiments, the heterologous promoter is any promoter that can be bound or activated by the Upc2, Ecm22, Upc2G888D, or Ecm22G790D transcription factor, or functional variant thereof. In some embodiments, the promoter comprises 2 DNA half sites comprised of 3-5 C/G combinations.

In some embodiments, the compound is an organic compound produced in nature by a living organism. In some embodiments, the compound is an organic compound or precursor produced by a metabolic pathway. In some embodiments, the metabolic pathway can be any metabolic pathway found naturally in a eukaryote or prokaryote. In some embodiments, the metabolic pathway can be any metabolic pathway found naturally in a eubacteria or archaebacteria. In some embodiments, the metabolic pathway produces a sesquiterpene, such as bisabolene or farnesene. Increasing the production of a compound comprises overproducing the compound. In some embodiments, the compound is any compound or precursor produced in the metabolic pathway shown in FIG. 1. In some embodiments, the precursor is farnesyl diphosphate (FPP) and the first biosynthetic enzyme is AgBIS.

In some embodiments, the compound is any compound or precursor, or any compound or precursor produced in the metabolic pathway, described in U.S. Provisional Patent Application Ser. No. 61/524,271; U.S. patent application Ser. Nos. 12/643,817; 12/644,531; 12/646,189; 13/318,474; 13/549,034; and, 13/274,244; and, PCT International Patent Application Nos. PCT/US2011/059784; PCT/US2012/031025; and, PCT/US2012/023182 (hereby incorporated by reference).

In some embodiments, the promoter that is weakly induced, not induced, or repressed by the transcription factor is the met3 or met25 promoter, or functional variant thereof, or any other promoter that is weakly induced, not induced, or repressed by the transcription factor.

In some embodiments, the third compound is squalene and the second biosynthetic enzyme is squalene synthase.

In some embodiments, the system is in a host cell or a cell-free or cell extract system. Any yeast host cell may be used in the present invention so long as it remains viable after being transformed with a sequence of nucleic acids. Preferably, the host cell is not adversely affected by the introduction of the necessary nucleic acid sequences, the subsequent expression of the proteins, or the resulting of any intermediates or compounds produced. Suitable yeast host cells are those of the *Saccharomyces* genus, including not limited to *S. cerevisiae, S. pastorianus*, and *S. carlsbergensis*.

In some embodiments, the genetic constructs described herein are stably integrated into the chromosome(s) of the host cell. In some embodiments, the genetic constructs described herein are stably integrated into the chromosome(s) of the host cell and where the ORFs are native to the host cell, the genetic constructs replace or substitute the native gene of the host cell. For example, the pErg9::Upc2 construct would replace the native pUpc2::Upc2 of the host cell and/or the pMet25::Erg9 construct would replace the native pErg9::Erg9 of the host cell.

In some embodiments, the system further comprises provides the necessary precursors to produce the desired compound and the genes of the metabolic pathway for producing the desired compound. The system also provides the expression machinery to transcribe and translate accordingly. When the system is in a host cell, the precursors are naturally produced by the host cell, or the host cell is engineered to produce the host cell, or the host cell is grown in a condition wherein the precursor is present, such as in excess, and the host cell is capable of uptaking or transporting the precursor into the inside of the host cell.

The present invention provides for a method of producing a compound, the method comprising: (a) providing a fungal host cell of the present invention, and (b) culturing the host cell under conditions in which the transcription factor is expressed; such that one or more compounds are produced, such as the first compound and optionally the third compound. In some embodiments, the providing step (a) comprises introducing one or more of the first polynucleotide, second polynucleotide, and third polynucleotide into the fungal host cell.

In some embodiments, the invention allows overproducing FPP, precursor of sesquiterpene synthase such as bisabolene synthase, farnesene synthase used to produce sesquiterpene such as bisabolene and farnesene respectively.

In a particular embodiment, the method overproduces comprises inserting between Erg9 promoter and Erg9 encoding sequence the encoding sequence of the ergosterol transcription factor Upc2, its allelic variant Upc2G888D, Ecm22 or its allelic variant Ecm22G790D fused to a terminator, a marker gene and followed by a weak promoter that is not responsive to any these transcription factors (e.g. Met3, Met25 promoters). The sesquiterpene synthase can be expressed under the control of one of the Upc2-(or Ecm22) induced promoters such as Erg2 or Erg11. The engineered gene can be inserted at the Erg2 or Erg11 locus using the strategy described herein, since both genes are essentials, in a single non-essential locus or multiple loci using ribosomal repeated sequence loci (NTS2; non transcribed sequence; Szostak and Wu, Plasmid. October; 2(4):536-54, 1979, hereby incorporated by reference). Finally, this approach will also benefit of the flux reduction in one of the ergosterol pathways (such as Erg9) will create an ergosterol limitation that will further induce the native Upc2 expression which can be amplified by the APFL.

This invention is not limited to this pathway and can be applied to multigene-engineered pathways since several promoters are induced by Upc2 or Ecm22 transcription factors and can be used to overexpress several genes. Furthermore, many transcription factors have been indentified in yeast (and other fungi) that could be used to design various APFL to enhance the production of native metabolites or precursors designated as starting molecule for engineered pathway. Finally some metabolic pathways and regulatory networks are conserved between fungi, such as the ergosterol pathway, the presented approach is readily transferable.

This approach does not require the use of plasmids, thus it offers the opportunity to overexpress several genes in a plasmid free context with high success rate since promoter from the induced pathway become great candidates. In addition since it does not require the use of plasmids, it can be easily transferred to various fungi, such as yeast strains. It allows generating rapidly strains that will overproduce various final products or precursors. Furthermore it also facilitates the selection of promoters for the design of an engineered pathway.

The APFL approach is applicable to many metabolic pathways that are under control of a transcription factor. It can be used to enhance endogenous pathways as well as engineer pathways. Finally, it offers new potentials for metabolic engineering in order to produce various high value metabolites, biofuels, pharmaceutical compounds, chemicals and several other products.

The use of APFL in fungi (such as yeast) allows enhancing the expression of a key transcription factor and associated metabolic pathway. Homologous recombination in yeast can be efficiently performed. The method comprises: (a) inserting in a target locus an induced promoter fused to the target transcription factor, (b) replacing the coding sequence of an induce gene in the native pathway by the selected transcription factor if the replaced gene is a not essential gene, and/or (c) inserting between the promoter and the ATG (starting codon) of the selected gene, the target transcription factor followed by a terminator, a selective marker and a new promoter (independent of the above transcription factor) allowing disconnecting gene expression from the APFL and regulating the level of expression independently of the APFL.

Since metabolic engineering in fungi (such as yeast) uses most of the time precursors from a native pathway to feed an engineered pathway, the insertion of the APFL construct could be used to block or reduce the natural use of a key precursor that is needed to feed the engineered pathway. In some embodiments, for a metabolic pathway that requires a lot of FPP (precursor in the ergosterol pathway), the APFL is inserted in the Erg9 Locus. The encoding sequence of the ergosterol transcription factor Upc2, its allelic variant Upc2G888D, Ecm22 or its allelic variant Ecm22G790D is fused to a terminator, a marker gene and followed by a weak promoter that is not responsive to these transcription factors (such as the Met3 or Met25 promoter) which is inserted between Erg9 promoter and Erg9 encoding sequence. This system increases the production of FPP and reduce its consumption by the native ergosterol pathway, and thus FPP accumulates. Alternatively, if the starting precursor for the engineered pathway is GPP, Erg20 would be the target locus instead of Erg9.

The engineered pathway will be optimized by using promoters that are induced by the above transcription factors fused to the engineered pathway genes allowing the overexpression of the engineered pathway. It can be done by inserting the entire engineered pathway in one locus, stepwise by gene replacement if the native pathway is not essential, by using one of the other approaches described herein, or by using plasmids (less preferred because of stability issues).

This method/technology offers rapid, simple and reliable approaches for pathway engineering in various fungal host cells, such as yeast host cells.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Figure 5:
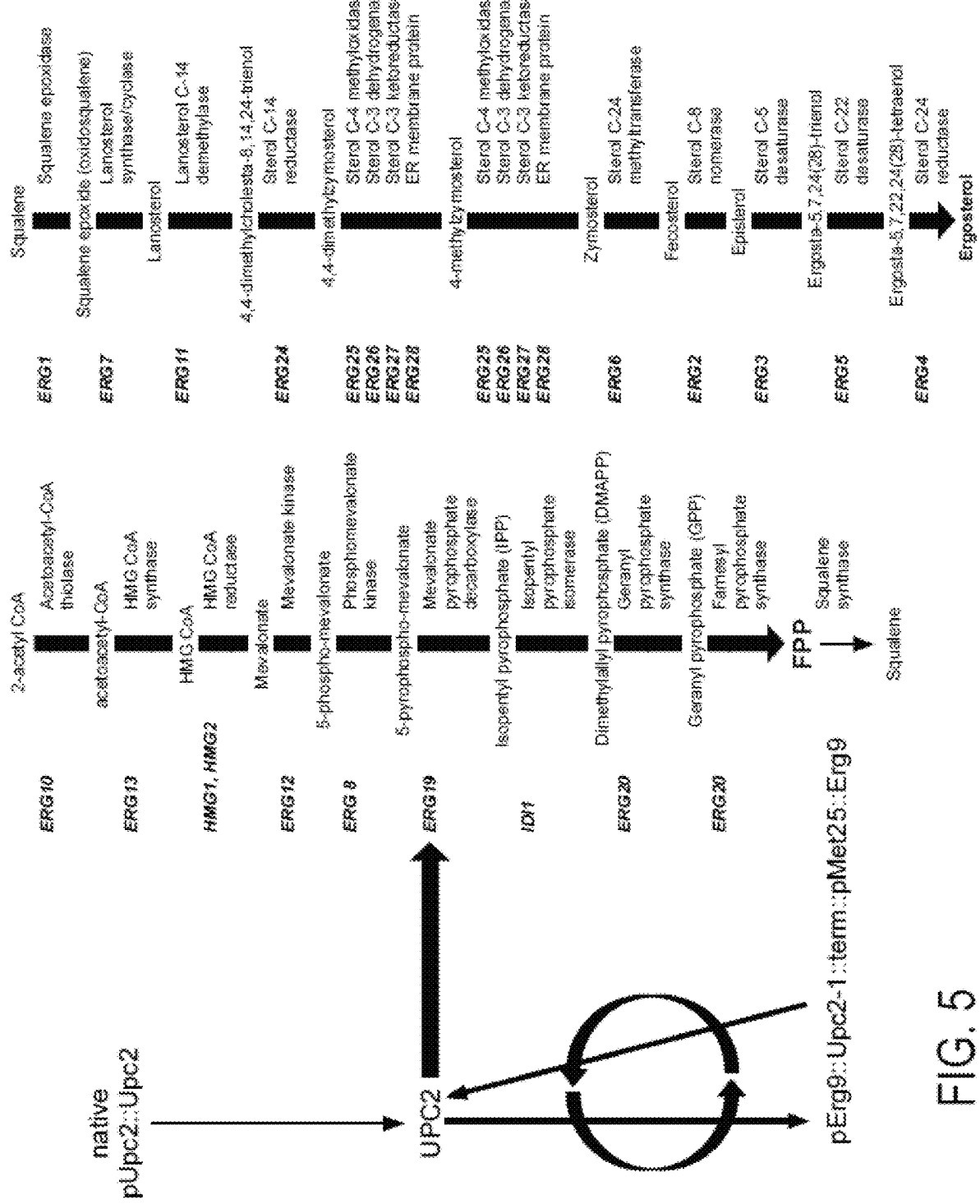
FIG. 5 shows the APFL approach to increase FPP availability in yeast.

A particular example of the invention for producing FPP is described in FIG. 5. The system comprises an expression cassette comprising the Upc2 ORF operably linked to the promoter of the erg9 gene, and the Erg9 ORF operably to the promoter of the met25 gene. The system provides 2-acetyl CoA precursor and the genes of the metabolic pathway for producing FPP (as shown in FIG. 5). The system provides the expression machinery to transcribe and translate accordingly. The system overproduces FPP.

Example 2

Figure 6:
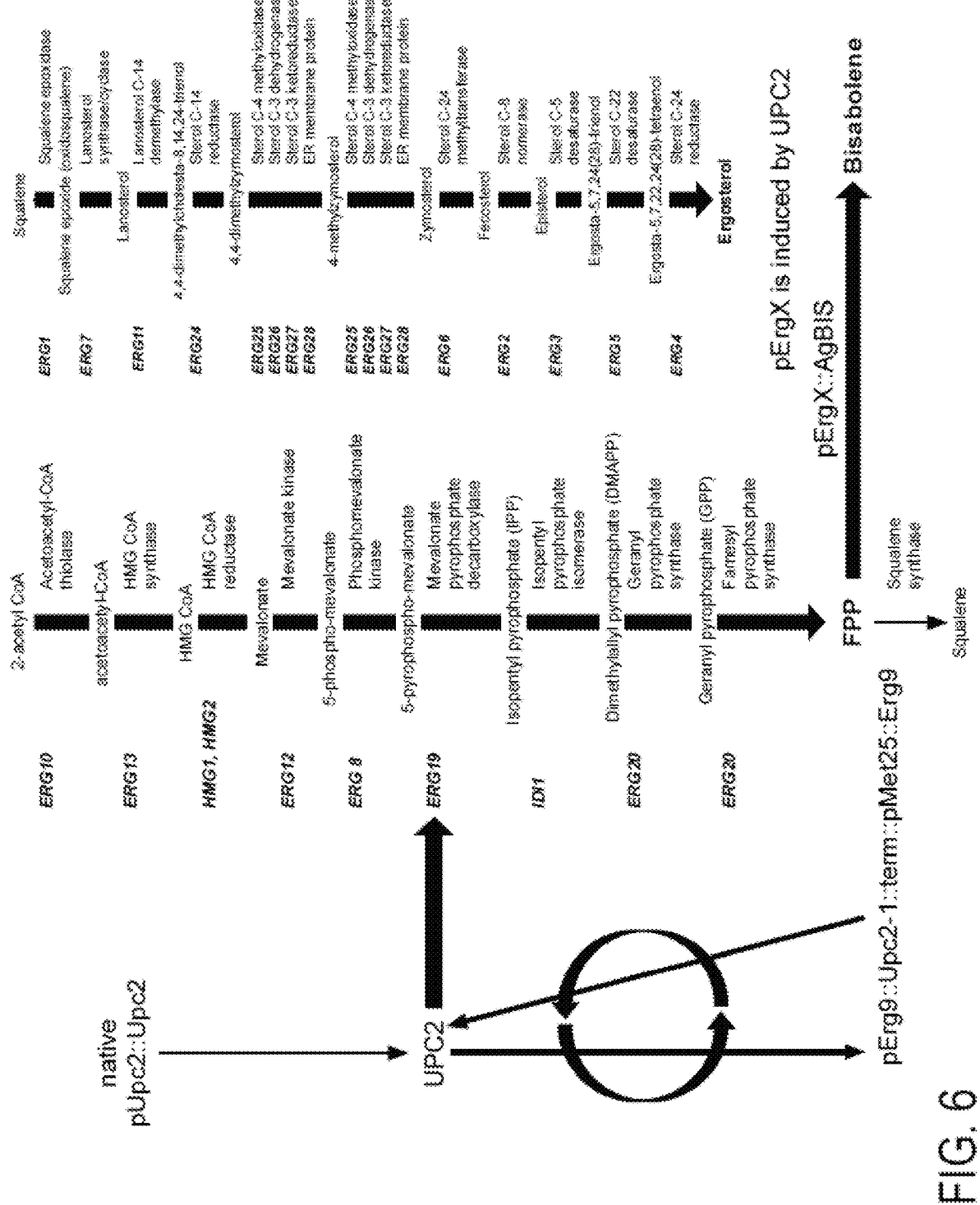
FIG. 6 shows the APFL approach to increase FPP availability in yeast and a system to produce bisabolene.

A particular example of the invention for producing bisabolene is described in FIG. 6. The system comprises an expression cassette comprising the Upc2 ORF operably linked to the promoter of the erg9 gene, and the Erg9 ORF operably to the promoter of the met25 gene. The system provides 2-acetyl CoA precursor and the genes of the metabolic pathway for producing FPP (as shown in FIG. 6). The system also provides an expression cassette comprising the AgBIS ORF operably linked to an erg promoter which is enhanced by Upc2. The system provides the expression machinery to transcribe and translate accordingly. The system overproduces bisabolene.

Example 3

Figure 7:
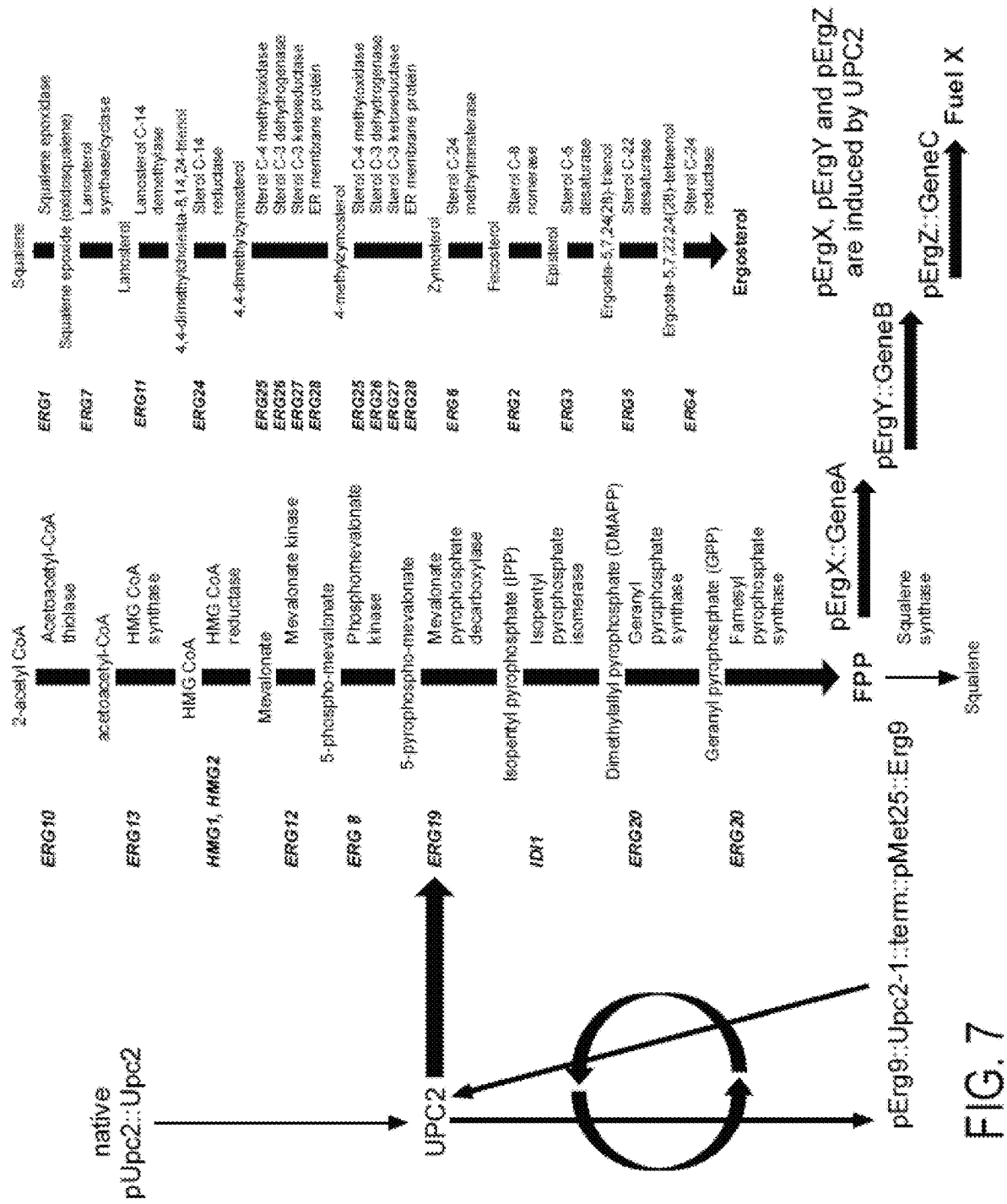
FIG. 7 shows the APFL approach to increase FPP availability in yeast and a system to produce a fuel X.

A particular example of the invention for producing a generic fuel X, which is synthesized using FPP as a precursor, is described in FIG. 7. The system comprises an expression cassette comprising the Upc2 ORF operably linked to the promoter of the erg9 gene, and the Erg9 ORF operably to the promoter of the met25 gene. The system provides 2-acetyl CoA precursor and the genes of the metabolic pathway for producing FPP (as shown in FIG. 7). The system also provides one or more expression cassettes comprising the genes encoding enzymes for catalyzing fuel X from FPP, wherein each gene is operably linked to an erg promoter which is enhanced by Upc2. The system provides the expression machinery to transcribe and translate accordingly. The system overproduces fuel X.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified fungal host cell, comprising: (a) a first polynucleotide encoding a fungal transcription factor operably linked to a first promoter that is native to the transcription factor, (b) a second polynucleotide encoding a first biosynthetic enzyme operably linked to a second promoter that is induced or activated by the transcription factor, wherein the first biosynthetic enzyme catalyzes a first reaction which produces a first compound from a second compound, and (c) a third polynucleotide encoding an expression cassette inserted between a polynucleotide encoding a second biosynthetic enzyme and a native promoter of the second biosynthetic enzyme, wherein the expression cassette comprises a polynucleotide encoding the fungal transcription factor, a third promoter that is induced at a level lower than the induction of the first promoter and the second promoter, and a terminator located between the polynucleotide encoding the fungal transcription factor and the third promoter;

such that the native promoter of the second biosynthetic enzyme is operatively linked to the polynucleotide encoding the fungal transcription factor, and the third promoter is operatively linked to the polynucleotide encoding the second biosynthetic enzyme; wherein the transcription factor is Upc2, Ecm22, Upc2G888D, or Ecm22G790D and the second biosynthetic enzyme catalyzes a second reaction that is downstream of the first reaction in a metabolic pathway.

2. The genetically modified fungal host cell of claim 1, wherein any two or all of the first polynucleotide, second nucleotide, and third polynucleotide are of the same polynucleotide molecule.

3. The genetically modified fungal host cell of claim 1, wherein the third promoter is a met3 or met25 promoter.

4. The genetically modified fungal host cell of claim 1, wherein the fungal host cell is a yeast host cell.

5. The genetically modified fungal host cell of claim 1, wherein the genetically modified fungal host cell overproduces the first compound.

6. The genetically modified fungal host cell of claim 5, wherein the first biosynthetic enzyme is ERG19, the second biosynthetic enzyme is ERG9, and the first compound is farnesyl diphosphate (FPP).

7. The genetically modified fungal host cell of claim 6, wherein the transcription factor is Upc2 or Upc2G888D.

8. A method of producing a first compound, the method comprising:
(a) providing a genetically modified fungal host cell of claim 1, and
(b) culturing the host cell under conditions in which the transcription factor is expressed;
such that the first compound is produced.

9. The method of claim 8, wherein any two or all of the first polynucleotide, second nucleotide, and third polynucleotide are the same polynucleotide.

10. The method of claim 8, wherein the second promoter that is induced or activated by the transcription factor is a erg9 promoter, or functional variant thereof.

11. The method of claim 8, wherein the third promoter that is induced at a level lower than the induction of the first promoter and the second promoter is a the met3 or met25 promoter, or functional variant thereof.

12. The method of claim 8, wherein the providing step (a) comprises introducing one or more of the first polynucleotide, second polynucleotide, and third polynucleotide into the host cell.

13. The method of claim 8, wherein the fungal host cell is a yeast host cell.

* * * * *